US009629549B2

(12) United States Patent
Hensley et al.

(10) Patent No.: US 9,629,549 B2
(45) Date of Patent: Apr. 25, 2017

(54) SYSTEMS FOR FUSION OF FLUORESCENCE MOLECULAR TOMOGRAPHY AND MAGNETIC RESONANCE IMAGES

(71) Applicant: Institute for Cancer Research, Philadelphia, PA (US)

(72) Inventors: Harvey Hensley, Newtown Square, PA (US); Navid Roder, Newtown Square, PA (US)

(73) Assignee: Institute for Cancer Research, Philadelphia, PA (US)

( * ) Notice: Subject to any disclaimer, the term of this patent is extended or adjusted under 35 U.S.C. 154(b) by 406 days.

(21) Appl. No.: 14/040,812

(22) Filed: Sep. 30, 2013

(65) Prior Publication Data

US 2014/0031669 A1    Jan. 30, 2014

Related U.S. Application Data

(63) Continuation of application No. PCT/US2012/031414, filed on Mar. 30, 2012.
(Continued)

(51) Int. Cl.
*A61B 5/05* (2006.01)
*A61B 5/00* (2006.01)
*A61B 5/055* (2006.01)

(52) U.S. Cl.
CPC .......... *A61B 5/0035* (2013.01); *A61B 5/0071* (2013.01); *A61B 5/055* (2013.01); *A61B 5/0555* (2013.01)

(58) Field of Classification Search
CPC ..... A61B 5/0035; A61B 5/055; A61B 5/0071; A61B 5/0555
See application file for complete search history.

(56) References Cited

U.S. PATENT DOCUMENTS

2004/0015062 A1*  1/2004  Ntziachristos ....... A61B 5/0073
                                                 600/312
2004/0249260 A1   12/2004  Wang et al.
(Continued)

FOREIGN PATENT DOCUMENTS

WO      2009150564      12/2009

OTHER PUBLICATIONS

Garanger et al. ("New Multifunctional Molecular Conjugate Vector for Targeting, Imaging, and Therapy of Tumors", Molecular Therapy, vol. 12, No. 6, Dec. 2005).*
(Continued)

Primary Examiner — Jonathan Cwern
(74) Attorney, Agent, or Firm — Stradley Ronon Stevens & Young, LLP

(57) ABSTRACT

Methods for imaging a tumor in an animal including labeling an organ in the animal with a first detectable label detectable by both fluorescence molecular tomography (FMT) and magnetic resonance (MR) and localized substantially exclusively to the organ, whereupon the labeled organ is capable of use as a first fiducial marker in an image of the animal; administering to the animal a detectably labeled probe that localizes substantially exclusively to a region of interest in the body of the animal; after labeling the organ and administering the detectably labeled probe, imaging the animal with a FMT imager to generate an FMT image, and imaging the animal with a MR imager to generate an MR image; and aligning the FMT and MR images using the first fiducial marker as a first reference point, thereby generating an image comprising a fusion of the FMT image and the MR image.

8 Claims, 15 Drawing Sheets

Related U.S. Application Data

(60) Provisional application No. 61/470,976, filed on Apr. 1, 2011.

(56) References Cited

U.S. PATENT DOCUMENTS

| | | |
|---|---|---|
| 2008/0219933 A1 | 9/2008 | Ntziachristos et al. |
| 2009/0000567 A1 | 1/2009 | Hadjioannou et al. |
| 2009/0080600 A1 | 3/2009 | Keller et al. |
| 2009/0150564 A1 | 6/2009 | Anbalagan et al. |
| 2011/0071388 A1 | 3/2011 | Yared et al. |

OTHER PUBLICATIONS

McCann, et al., "Combined magnetic resonance and fluorescence imaging of the living mouse brain reveals glioma response to chemotherapy", Neuroimage, Apr. 1, 2009; 45(2):360-369.

Connolly, et al., "Female Mice Chimeric for Expression of the Simian Virus 40 TAg under Control of the MISIIR Promotor Develop Epithelial Ovarian Cancer", Cancer Research, Mar. 15, 2003; 63:1389-1397.

Hensley, et al., "Magnetic Resonance Imaging for Detection and Determination of Tumor Volume in a Genetically Engineered Mouse Model of Ovarian Cancer", Cancer Biology & Therapy, Nov. 2007, 6:11, 1717-1725.

International Search Report dated Oct. 5, 2012, from parent application PCT/US12/31414.

\* cited by examiner

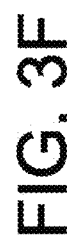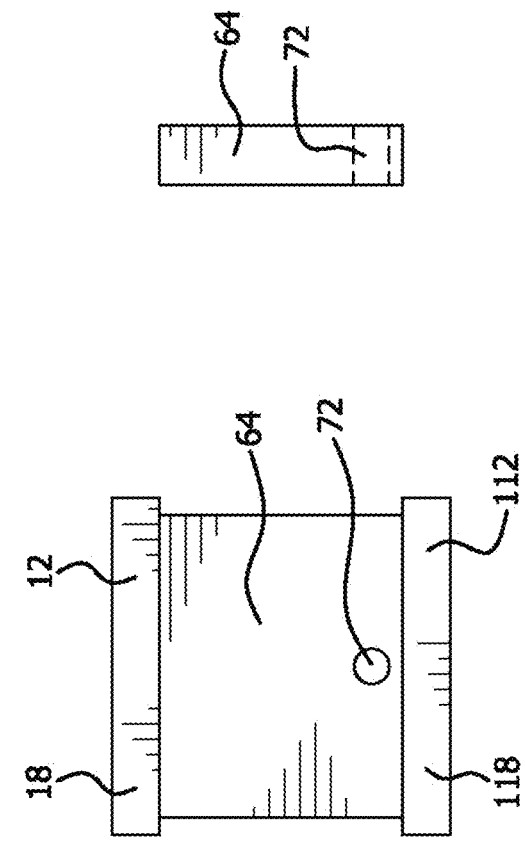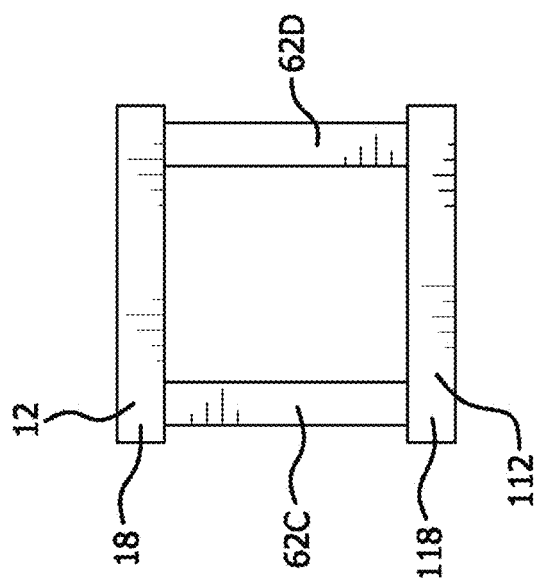
FIG. 3F
FIG. 3E
FIG. 3D

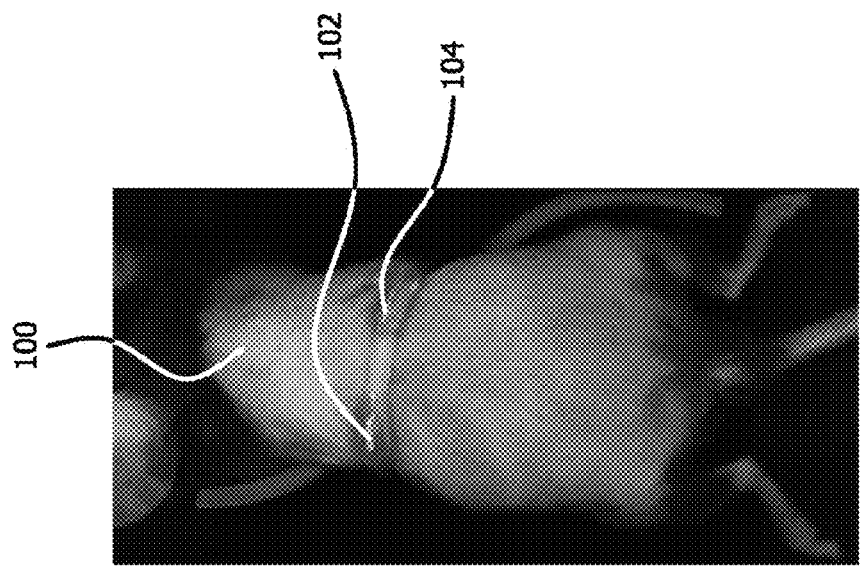
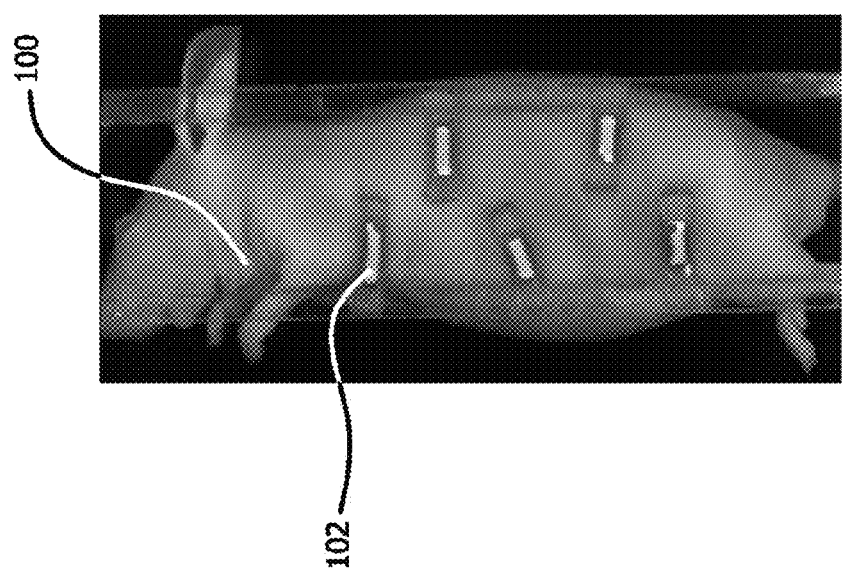
FIG. 8

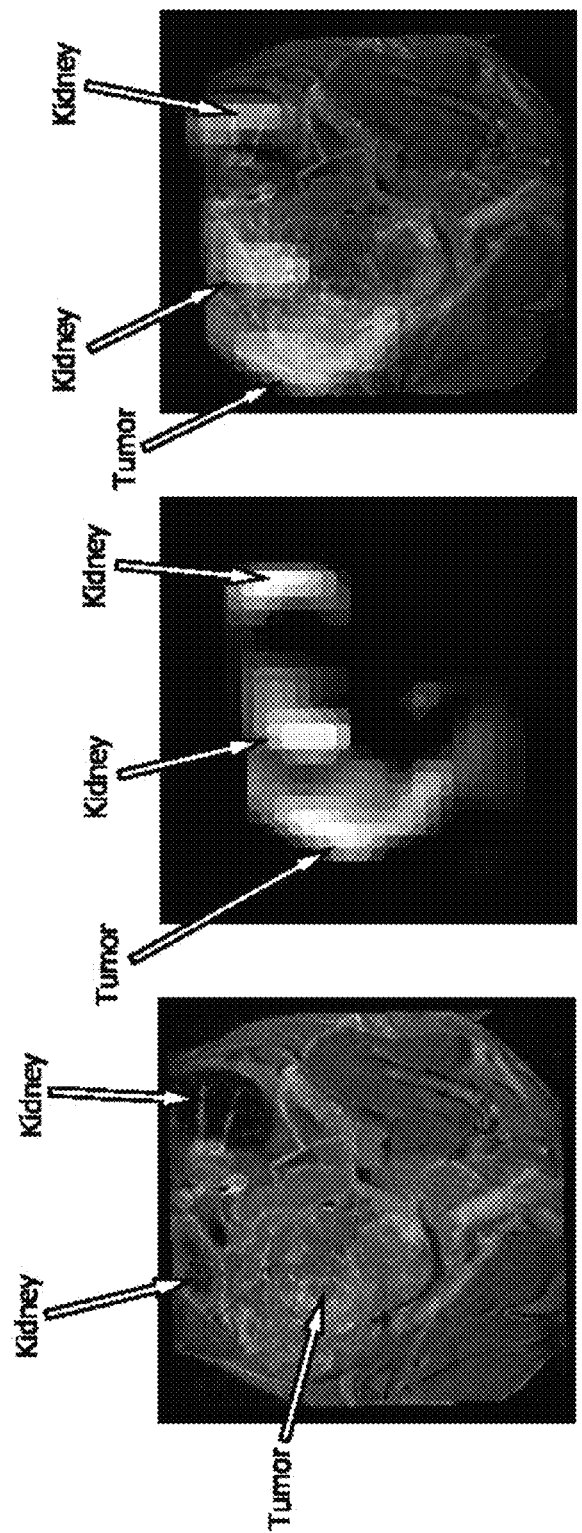

SYSTEMS FOR FUSION OF FLUORESCENCE MOLECULAR TOMOGRAPHY AND MAGNETIC RESONANCE IMAGES

CROSS REFERENCE TO RELATED APPLICATIONS

This application is a continuation of PCT Application No. PCT/US2012/031414, filed on Mar. 30, 2012, and claims priority to U.S. Provisional Application No. 61/470,976, filed on Apr. 1, 2011, the contents of which are incorporated by reference herein, in their entirety and for all purposes.

FIELD OF THE INVENTION

The invention relates generally to the field of imaging. More particularly, the invention relates to cassettes for holding animals in a magnetic resonance imager such as a vertical bore magnetic resonance imager, as well as to systems and methods for imaging animals in fluorescent molecular tomographic and magnetic resonance imagers.

BACKGROUND OF THE INVENTION

Various publications, including patents, published patent applications, technical articles, and scholarly articles, are cited throughout the specification. Each of these cited publications is incorporated by reference in this document, in its entirety and for all purposes.

Fluorescent molecular tomography (FMT) is an imaging technique that allows for fluorescence-based imaging of the inside of live animals. Fluorescence measurements are obtained, and the three-dimensional distribution of fluorescent agents is reconstructed. FMT is quantitative and allows for measurements of fluorophore intensity, e.g., marker concentration, at locations within the animal. FMT is limited, however, insofar as it lacks the ability to generate precise anatomical details of fluorescent tissue and the surrounding tissue.

Magnetic resonance imaging (MRI), in contrast to FMT, is able to provide high resolution three dimensional images of anatomical structures. Magnetic resonance imaging is limited, however, insofar as it lacks fluorescent probe detection sensitivity. Therefore, it is desirable to combine FMT and MRI to achieve detailed images of fluorescence-labeled tissue in the proper anatomical context. Combined FMT and MRI imaging is valuable as a research and diagnostic tool, particularly in the area of oncology (McCann C M et al. (2009) Neuroimage 45:360-9).

As FMT and MRI are separate techniques carried out using separate machines, image alignment from both analyses is not straight forward. The incompatibility of platforms to hold animals in place during imaging with each technique is a primary contributor to the problems of image alignment. Incompatibility necessitates that an animal be imaged using FMT on one platform, and then moved to another platform for MRI imaging. It is difficult and time consuming to realign the animal in the same position and orientation between the FMT and MRI platforms. In addition, movement of the animal may cause shifting of internal organs, further contributing to alignment difficulties. A need exists to reduce or avoid the requirement to move the animal, and to enhance the efficiency and accuracy of FMT-MRI image alignment.

SUMMARY OF THE INVENTION

To meet these and other needs, and in view of its purposes, the present invention features cassettes for fluorescent molecular tomography and magnetic resonance imaging of an animal. In some embodiments, the cassettes comprise a top planar frame having a first window and a bottom planar frame having a second window aligned with the first window. The cassettes have a length, width, and height that allow the cassettes to fit inside the radio-frequency coil of a vertical bore magnetic resonance imager, and that define a chamber for holding an animal in a desired position during fluorescent molecular tomography and magnetic resonance imaging of the animal. The first and second window may comprise polyethylene terephthalate, and the top and bottom frame may comprise polymethyl methacrylate. The cassette may be adapted to fit in a fluorescence molecular tomography holder.

The cassette may further comprise a plurality of wells for containing a fiducial marker, and in some aspects, one or more fiducial markers are contained within at least one of the plurality of wells. The one or more fiducial markers are preferably detectable by both a fluorescent molecular tomography imager and a magnetic resonance imager.

The invention also features systems comprising a cassette such as the cassettes described in this specification, a fluorescent molecular tomography imager, a magnetic resonance imager, and a processor programmed to combine data obtained from the fluorescent molecular tomography imager and the magnetic resonance imager to generate an image comprising a fusion of a fluorescent molecular tomography image and a magnetic resonance image. The system may further comprise a holder for a fluorescent molecular tomography imager, and the cassette may fit within the holder to allow fluorescent molecular tomography imaging and a magnetic resonance imaging of an animal in the cassette without repositioning the animal and without removing the animal from the cassette. The system may comprise markers for affixing to the exterior of an animal, which markers may comprise fiducial markers. In some aspects, the marker comprises a band comprising a fiducial marker, with the band adapted to be placed around the exterior of an animal such as a mouse, and the fiducial marker detectable by a fluorescent molecular tomography imager and a magnetic resonance imager.

The invention also features methods for fluorescent molecular tomography and magnetic resonance imaging of an animal. In some embodiments, the methods generally comprise imaging an animal to which an organ-specific label such as a kidney label and one or more probes has been administered with a fluorescence molecular tomography imager, imaging the animal with a magnetic resonance imager, and combining the data obtained from the fluorescence molecular tomography imager and the magnetic resonance imager to generate an image comprising a fusion of a fluorescent molecular tomography image and a magnetic resonance image. The magnetic resonance imager is preferably a vertical bore magnetic resonance imager. The animal is preferably held in place by a cassette such as a cassette described in this specification during the imaging of the animal with the magnetic resonance imager, and in some aspects, during the imaging of the animal with the fluorescence molecular tomography imager.

The organ-specific label may comprise an agent that binds to phosphatidylserine. The probe may specifically localize to a cancer marker. The probe may specifically localize to an ovarian cancer marker. The ovarian cancer marker may be a cathepsin expressed in an ovarian cancer cell, or a matrix metalloproteinase expressed in an ovarian cancer cell, and/ or an integrin expressed in an ovarian cancer cell. The integrin is alpha v beta 3. The probe preferably comprises a detectable label.

In some embodiments, the methods generally comprise imaging an animal to which one or more fiducial markers have been attached and to which one or more probes have been administered with a fluorescence molecular tomography imager, imaging the animal with a magnetic resonance imager, and combining the data obtained from the fluorescence molecular tomography imager and the magnetic resonance imager to generate an image comprising a fusion of a fluorescent molecular tomography image and a magnetic resonance image. The magnetic resonance imager is preferably a vertical bore magnetic resonance imager. The animal is preferably held in place by a cassette such as a cassette described in this specification during the imaging of the animal with the magnetic resonance imager, and in some aspects, during the imaging of the animal with the fluorescence molecular tomography imager. The fiducial markers attached to the animal may be in a band wrapped around the animal, the band containing the fiducial markers. The fiducial markers may comprise a detectable label.

The probe may specifically localize to a cancer marker. The probe may specifically localize to an ovarian cancer marker. The ovarian cancer marker may be a cathepsin expressed in an ovarian cancer cell, or a matrix metalloproteinase expressed in an ovarian cancer cell, and/or an integrin expressed in an ovarian cancer cell. The integrin is alpha v beta 3. The probe preferably comprises a detectable label.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 3D shows a perspective of the distal end of a cassette using posts. FIG. 3E shows a perspective of the distal end of a cassette using a back wall. FIG. 3F shows a side perspective of the back wall shown in FIG. 3E.

FIG. 8 shows a FMT-MRI transfer cassette with a mouse having fiducial markers;

FIGS. 11A-11C show MRI, FMT, and FMT-MRI fused images. A tumor bearing TgMISIIR-TAg (TAg+) mouse was injected with ProSense® 680 and AnnexinVivo 750 24 and 2 hours prior to imaging, respectively. FIG. 11A shows the MRI image. FIG. 11B shows the FMT image. FIG. 11C shows the fused image of FIG. 11A and FIG. 11B. Both kidneys and a large tumor on the right side of the image are circled and labeled on all three images. Note the strong accumulation of probe on the right side of the tumor. The fluorescent images were acquired in the 680 channel for Prosense® 680, and 750 channel for Annexinvivo 750, and the merged image was created with the AMIDE™ software.

FIG. 12A shows the MR image with the ovarian tumors and the kidneys labeled. FIG. 12B shows the corresponding FMT image, and FIG. 12C shows fused images showing merged fluorescent signals detected in the 680 (ProSense® or ProSense® Control) and 750 (AnnexinVivo) channels.

FIG. 13A shows the MR image with the ovarian tumors and the kidneys labeled. FIG. 13B shows the corresponding FMT image, and FIG. 13C shows fused images showing merged fluorescent signals detected in the 680 (Integrisense 680) and 750 (AnnexinVivo) channels.

FIG. 14A shows a slice from the MRI dataset. FIG. 14B shows a corresponding slice from the FMT dataset showing widespread distribution of the MMPSense® 680 probe. FIG. 14C shows FMT images with AnnexinVivo 750 in the kidneys, and MMPSense® 680 distribution masked with the corresponding region of the tumors taken from the MRI dataset. FIG. 14D shows fused FMT and MRI images.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided in this document.

As used in this document, the singular forms "a," "an," and "the" include plural referents unless expressly stated otherwise.

The term "about" includes variations of 20%, 10%, 5%, 2%, 1%, 0.5%, or 0.1% higher or lower than the specified value.

The cassettes, systems, and methods described or exemplified in this document may be used on any animal, with small mammals such as laboratory mammals being preferred. Non-limiting examples of laboratory mammals include mice and rats, with mice being preferred.

The invention features cassettes that gently hold an animal in place for imaging in a vertical bore magnetic resonance (MR) imager. The cassettes may be modular in nature, to allow for changes in length, width, and height to accommodate different sized animals. In some preferred aspects, the cassettes may be inserted into holders or other cassettes that are used for imaging in a fluorescence molecular tomography (FMT) imager such that the animal need not be removed from the cassette or repositioned to be imaged by the FMT or the MR imager. The cassettes may be useful for research and diagnostic applications.

Figure 1:
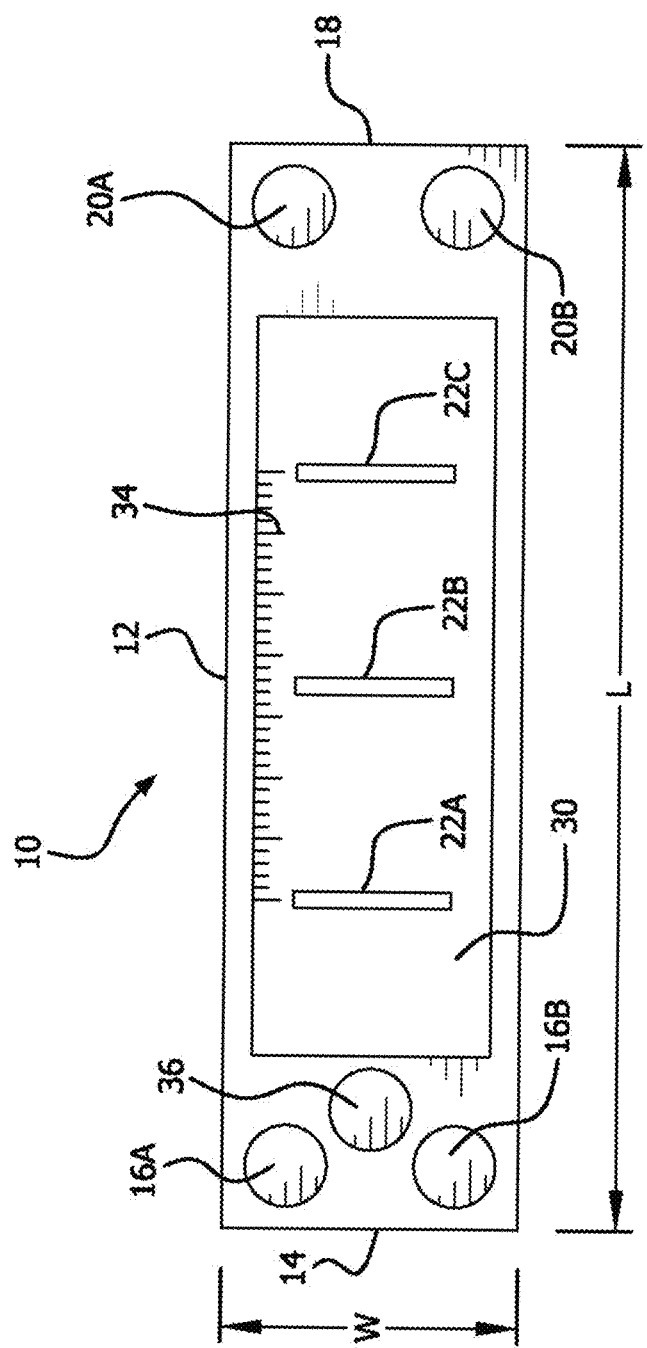
FIG. 1 shows a perspective of a top frame of a cassette.

In some aspects, a cassette 10 has a substantially planar top frame 12 as shown in FIG. 1. FIG. 1 shows a top perspective of the top frame 12. The top frame 12 has a proximal end 14 and a distal end 18, and has a width W and a length L, and has a thickness Th. The top frame 12 may have a window 30 as shown in FIG. 1, although the entire top frame 12 may comprise the window 30. In some aspects, the window 30 may optionally have at least one chamber or well 22, or a plurality of chambers or wells 22, which may be used to house fiducial markers. In some aspects, the window 30 may optionally have a plurality of hatch marks 34, which may be used to house fiducial markers, and which may be used for measurements. FIG. 1 shows three wells 22A, 22B, and 22C, although fewer or more than three wells 22 may be present.

On the underside of the top frame 12, the proximal end 14 has one or more bores 16A and 16B. The bores 16A and 16B may be used to fasten a post 62 or a front wall 63 to the top frame 12. The bores 16A and 16B may be any shape, and substantially circular bores 16A and 16B are shown in FIG. 1. A single bore 16 may be used, and the single bore 16 may be transverse substantially across the width W of the proximal end 14, and may be used, for example, to fasten the front wall 63 to the top frame 12. The bores 16A and 16B may extend partially into, but not through, the top frame 12, or the bores 16A and 16B may extend entirely through the top frame 12. The post 62 or front wall 63 may friction fit into the bores 16A and 16B to allow assembly and disassembly of the cassette 10, though the post 62 or front wall 63 may be affixed to the bores 16A and 16B. The post 62 may be a screw such as a nylon 6-32 screw.

The top frame 12 may optionally have a bracket 42 to hold or otherwise fasten a hose 40, such as the hose 40 for delivering a gas such as an anesthetic gas or oxygen, to the cassette 10. The top frame 12 may optionally have a connector 36 on the top side of the top frame 12 to connect a hose 40 for delivering a gas to the cassette 10. The connector 36 has a lumen through it to allow the gas to pass from the hose 40 into the chamber 70 of the cassette 10 where an animal is housed for imaging.

On the underside of the top frame 12, the distal end 18 may have one or more bores 20A and 20B. The bores 20A and 20B may be used to fasten the post 62 or a back wall 64 to the top frame 12. The bores 20A and 20B may be any shape, and substantially circular bores 20A and 20B are shown in FIG. 1. A single bore 20 may be used, and the single bore 20 may be transverse substantially across the width W of the distal end 18, and may be used, for example, to fasten the back wall 64 to the top frame 12. The bores 20A and 20B may extend partially into, but not through, the top frame 12, or the bores 20A and 20B may extend entirely through the top frame 12. The post 62 or back wall 64 may friction fit into the bores 20A and 20B to allow assembly of the cassette 10, although the post 62 or back wall 64 may be affixed to the bores 20A and 20B. The post 62 may be a screw such as a nylon 6-32 screw.

In some aspects, the cassette 10 has a substantially planar bottom frame 112 (see FIG. 2), which may have substantially the same configuration as the top frame 12 as shown in FIG. 1. For example, the bottom frame 112 has a proximal end 114 and a distal end 118, and has a width W and a length L, and has a thickness Th. The bottom frame 112 may have a window 130, although the entire bottom frame 112 may comprise the window 130. In some aspects, the window 130 may optionally have at least one well 122, or a plurality of chambers or wells 122A, 122B, and 122C, which may be used to house fiducial markers. In some aspects, the window 130 may optionally have a plurality of hatch marks 134, which may be used to house fiducial markers, and which may be used for measurements.

On the topside of the bottom frame 112 (which is positioned in the cassette 10 in the same direction as the topside of the top frame 12), the proximal end 114 may have one or more bores 116A and 116B. The bores 116A and 116B may be used to fasten the post 62 or the front wall 63 to the bottom frame 112. The bores 116A and 116B may be any shape. A single bore 116 may be used, and the single bore 116 may be transverse substantially across the width W of the proximal end 114, and may be used, for example, to fasten the front wall 63 to the bottom frame 112. The bores 116A and 116B may extend partially into, but not through, the bottom frame 112, or the bores 116A and 116B may extend entirely through the bottom frame 112. The post 62 or front wall 63 may friction fit into the bores 116A and 116B to allow assembly of the cassette 10, although the post 62 or front wall 63 may be affixed to the bores 116A and 116B. The bottom frame 112 may optionally have a bracket 142 to hold or otherwise fasten the hose 40, such as the hose 40 for delivering a gas such as an anesthetic gas or oxygen, to the cassette 10.

On the topside of the bottom frame 112 (which is positioned in the cassette 10 in the same direction as the topside of the top frame 12), the distal end 118 may have one or more bores 120A and 120B. The bores 120A and 120B may be used to fasten the post 62 or the back wall 64 to the bottom frame 112. The bores 120A and 120B may be any shape. A single bore 120 may be used, and the single bore 120 may be transverse substantially across the width W of the distal end 118, and may be used, for example, to fasten the back wall 64 to the bottom frame 112. The bores 120A and 120B may extend partially into, but not through, the bottom frame 112, or the bores 120A and 120B may extend entirely through the bottom frame 112. The post 62 or back wall 64 may friction fit into the bores 120A and 120B to allow assembly of the cassette 10, although the post 62 or back wall 64 may be affixed to the bores 120A and 120B.

Figure 2:
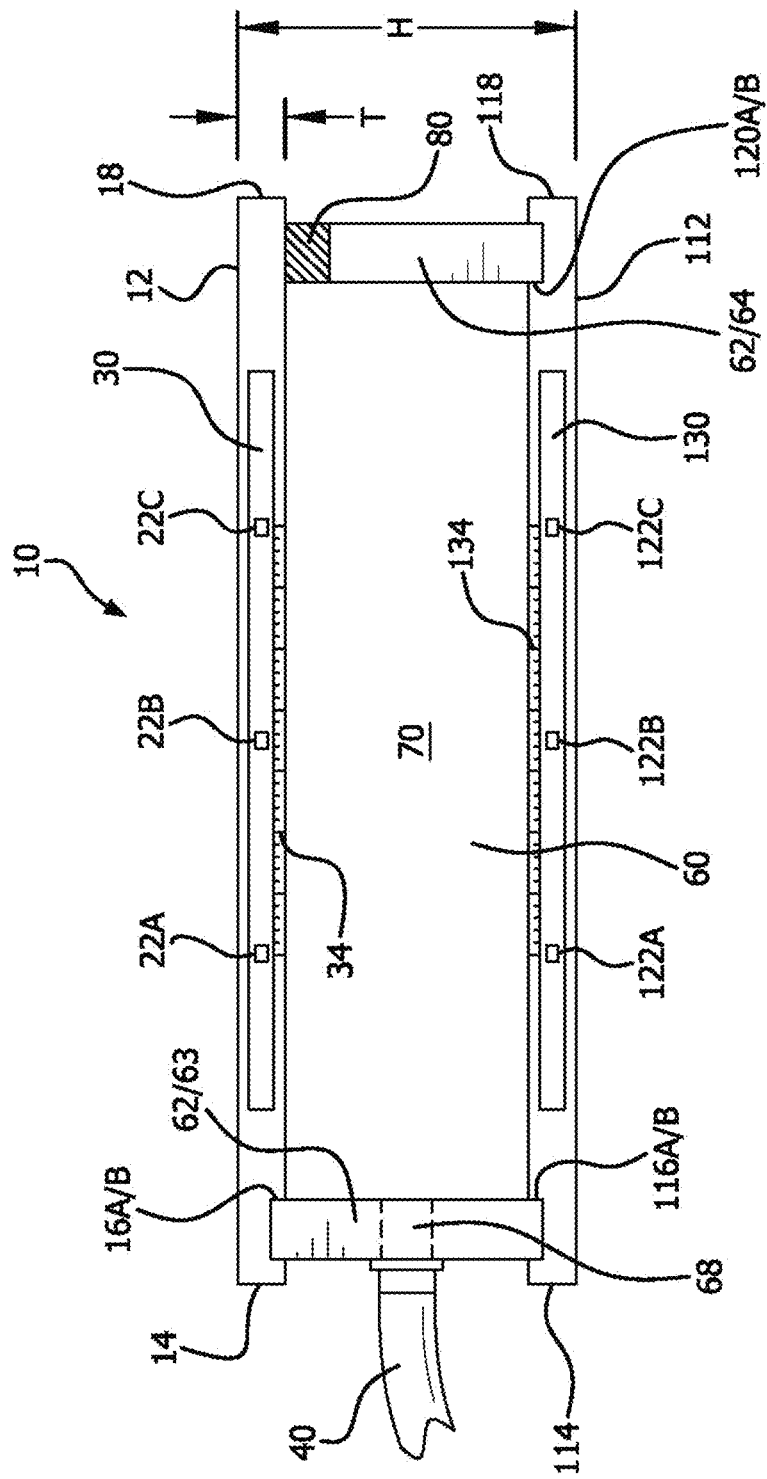
FIG. 2 shows a side perspective of a cassette.

A side perspective of a cassette 10 is shown in FIG. 2. FIG. 2 shows the top frame 12 and the bottom frame 112 assembled into the cassette 10 by way of the post 62/front wall 63 and the post 62/back wall 64. The side perspective of FIG. 2 shows the thickness Th of each of the top frame 12 and the bottom frame 112, and also shows a height H of the cassette 10. FIG. 2 also shows the windows 30 and 130, the plurality of wells 22A-22C on the top frame 12, the plurality of wells 122A-122C on the bottom frame 112, the plurality of hatch marks 34 on the top frame 12, and the plurality of hatch marks 134 on the bottom frame 112. The hatch marks 34 and 134 may be raised or depressed, and may be wells or chambers.

FIG. 2 also illustrates some possible alternative features of the cassette 10. It is to be understood that such alternative features may or may not be present on certain embodiments of the cassette 10, and FIG. 2 demonstrates combinations of such features for illustration purposes. In some aspects, the cassette 10 may comprise one or more hinges 80 to connect the top frame 12 to the post 62, front wall 63, and/or back wall 64. FIG. 2 shows the hinge 80 at the distal end 18 of the top frame 12, although the hinge 80 may be present at the proximal end 14 of the top frame 12 as well, or instead. The hinge 80 may thus permit the top frame 12 to be opened or closed. The hinge 80 may also be used with the bottom frame 112, and be present at the proximal end 114 and/or the distal end 118 of the bottom frame 112. In some aspects, the cassette 10 may have a side wall 60, although in preferred aspects the cassette 10 does not have a side wall 60. FIG. 2 shows an optional side wall 60.

FIG. 2 also shows an example of a friction fit between the top frame 12, bottom frame 112, and the post 62/front wall 63. As shown, the post 62/front wall 63 is positioned in the bore 16A/B partially extending into the top frame 12 and in the bore 116A/B partially extending into the bottom frame 112. In some aspects where the front wall 63 is used, the front wall 63 may have a bore 68 through the front wall 63 that allows a gas such as an anesthetic gas or oxygen to flow from the hose 40 into the animal housing chamber 70 of the cassette 10.

The cassette 10 may be configured for modular assembly with posts 62, front walls 63, or back walls 64, and into various heights H with different sized posts 62, front walls 63, or back walls 64, or even different sized top frames 12 and bottom frames 112, to accommodate larger and smaller animals.

Figure 3A:
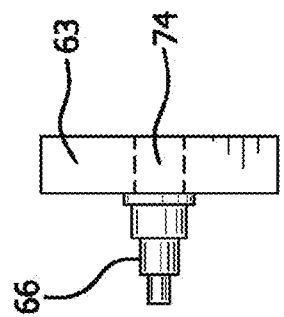
FIG. 3A shows a perspective of the proximal end of a cassette using posts.
Figure 3B:
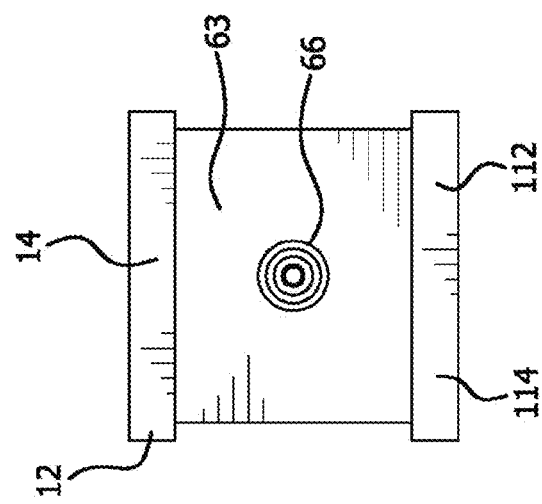
FIG. 3B shows a perspective of the proximal end of a cassette using a front wall.
Figure 3C:
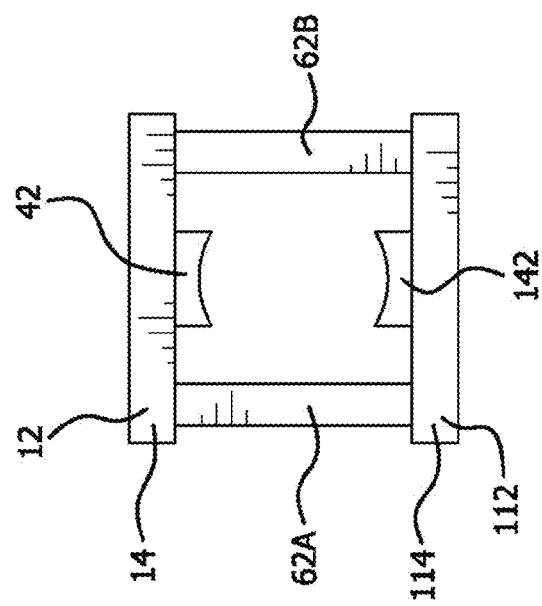
FIG. 3C shows a side perspective of the front wall shown in FIG. 3B.

FIG. 3 shows perspectives of the proximal 14/114 and distal 18/118 ends of the cassette 10. In FIG. 3A, a proximal view of the cassette 10 shows posts 62A and 62B connected to the top frame 12 and the bottom frame 112 of the cassette 10. The bracket 42 is shown on the top frame 112. In FIG. 3B, a proximal view of the cassette 10 shows the front wall 63 connected to the top frame 12 and the bottom frame 112 of the cassette 10. The front wall 63 is shown having a connector 66 for the hose 40 (not shown) to attach to the cassette 10. The connector 66 has a lumen through it to allow a gas to pass from the hose 40 into the chamber 70 of the cassette 10 where an animal is housed for imaging studies, and the lumen aligns with a front wall bore 74 through the front wall 63. FIG. 3C shows a side perspective of the front wall 63 with the connector 66 extending proximally and aligning with the front wall bore 74.

In FIG. 3D, a distal view of the cassette 10 shows the posts 62C and 62D connected to the top frame 12 and the bottom frame 112 of the cassette 10. In FIG. 3E, a distal view of the cassette 10 shows the back wall 64 connected to the top frame 12 and the bottom frame 112 of the cassette 10. The back wall 64 has a back wall bore 72 through which the tail of an animal may be inserted and passed through. FIG. 3F shows a side perspective of the back wall 64 with the back wall bore 72 extending through the back wall 64.

Figure 4A:
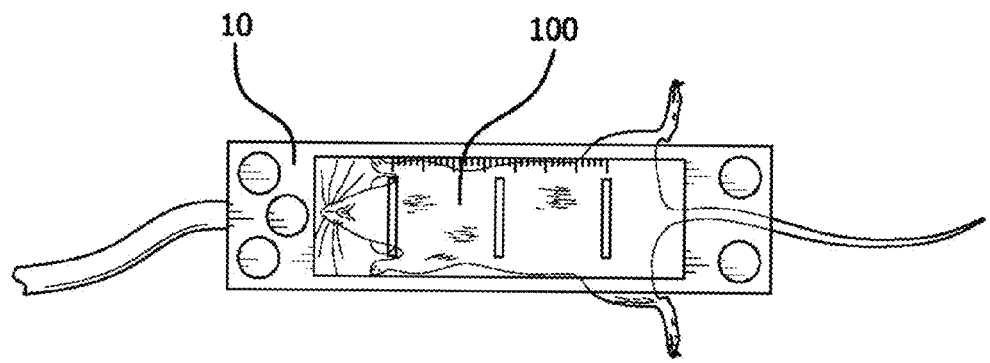
FIG. 4A shows an image of a cassette holding a mouse from a top perspective.
Figure 4B:
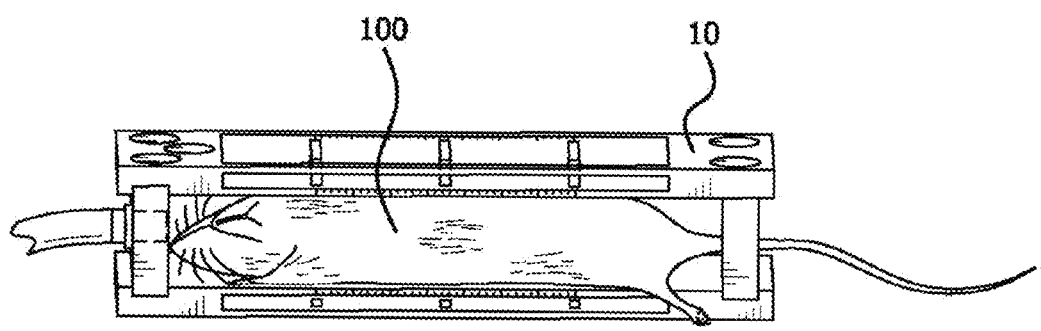
FIG. 4B shows an image of a cassette holding a mouse from a side perspective.

Images of an embodiment of the cassette 10 are shown in FIG. 4A and FIG. 4B. In FIG. 4A, a top perspective of the cassette 10 is shown with a mouse 100 held in place within the chamber 70. The cassette 10 shown in FIG. 4A does not include side walls, and the rear legs of the mouse 100 are shown extending out from the cassette 10. In FIG. 4B, a side perspective of the cassette 10 is shown with the mouse 100 held in place within the chamber 70.

The cassette 10 and its components can be fabricated from any suitable material or combination of materials. Different components of the cassette 10 (e.g., post 62, top frame 12, window 30, etc.) may be fabricated from different materials. The window 30 and window 130 may comprise glass, plastic, resin, or polymers such as acrylic polycarbonate, polypropylene, polyurethane, polyethylene terephthalate (e.g., Mylar® material available from DuPont Teijin Films, Wilmington, Del.), and polymethyl methacrylate (e.g., Lucite® material available from Lucite Int'l, Inc., Cordova, Tenn.). Other components may be fabricated from glass, plastic, resin, polymers, wood, rubber, ceramic, composite materials, or any combination thereof. The top frame 12, bottom frame 112, window 30, and/or window 130 may have an antireflective coating. The material is preferably compatible with both FMT and MR imagers.

The window 30 and window 130 are preferably fabricated from a material that allows electromagnetic radiation to pass through the window 30 and window 130 in a substantially un-attenuated form. The window 30 and window 130 may allow any type of radiation to pass through, including but not limited to X-rays, alpha rays, beta rays, gamma rays, positron rays, visible light, near-infrared light, far-infrared light, infrared light, ultraviolet light, radio waves, and microwaves.

The cassette 10 may have any suitable width W. The width W may range, for example, from about 2 cm to about 5 cm, from about 2 cm to about 4 cm, or from about 2 cm to about 3 cm, with about 2.5 cm preferred. Wider cassettes 10 may be used with larger animals. The cassette 10 may have any suitable length L. The length L may range, for example, from about 7 cm to about 15 cm, from about 8 cm to about 11 cm, from about 9 cm to about 12 cm, or from about 9 cm to about 11 cm, with about 10 cm preferred. Longer cassettes 10 may be used with larger animals. The thickness Th of the top frame 12 and the bottom frame 112 may be from about 0.1 mm to about 5 mm, from about 1 mm to about 4 mm, or from about 2 mm to about 4 mm, with about 3.5 mm preferred. The thickness of the post 62, front wall 63, or back wall 64 may be from about 5 mm to about 9 mm, or from about 6 mm to about 8 mm, with about 7 mm preferred.

The cassette 10 may have any suitable height H. The height H may range, for example, from about 0.5 cm to about 5 cm, from about 1 cm to about 4 cm, or from about 1 cm to about 3 cm, with about 2 cm preferred. The height H may be static, or may be adjustable, for example, by using smaller or larger posts 62 and/or front walls 63 and back walls 64, or by compressing the top frame 12 and/or bottom frame 112 (e.g., pushing the posts 62, front wall 63, or back wall 64 further into or through the one or more bores 16, 116, 20, or 120). The height H is such that an animal may be held in place by gentle compression of the animal between the top frame 12 and the bottom frame 112 of the cassette 10.

Figure 5:
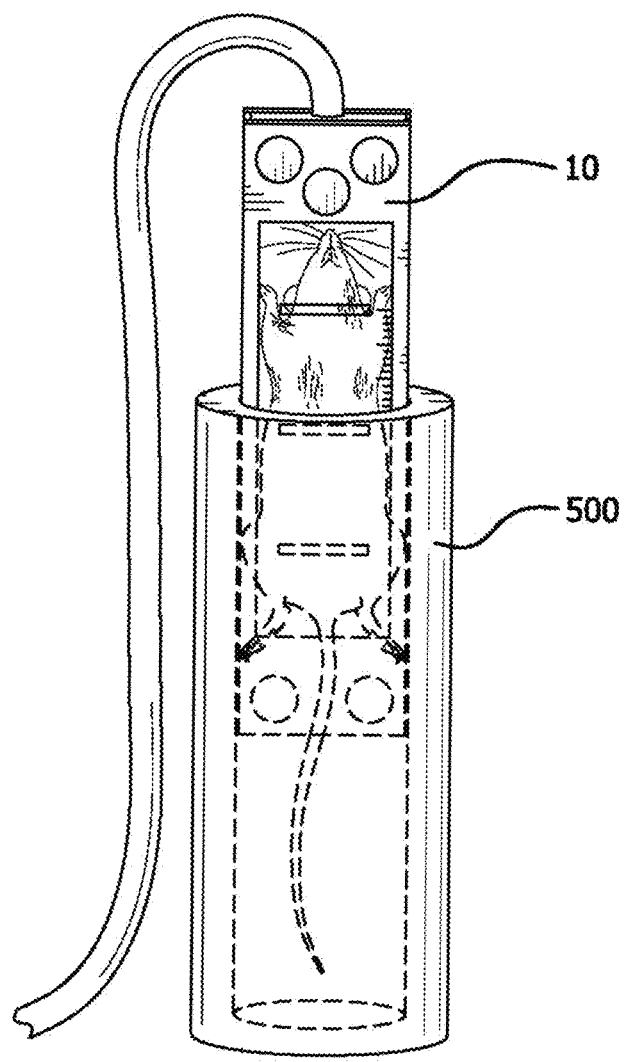
FIG. 5 shows a cassette in the radio frequency coil of a vertical-bore MRI system.

The cassette 10 may be used with any imaging system, and is preferably used in a magnetic resonance imager. More preferably, the cassette 10 is used with a vertical bore magnetic resonance imager such as a Bruker vertical bore system. An example of the use of the cassette 10 in a vertical bore magnetic resonance imager is shown in FIG. 5.

Figure 6:
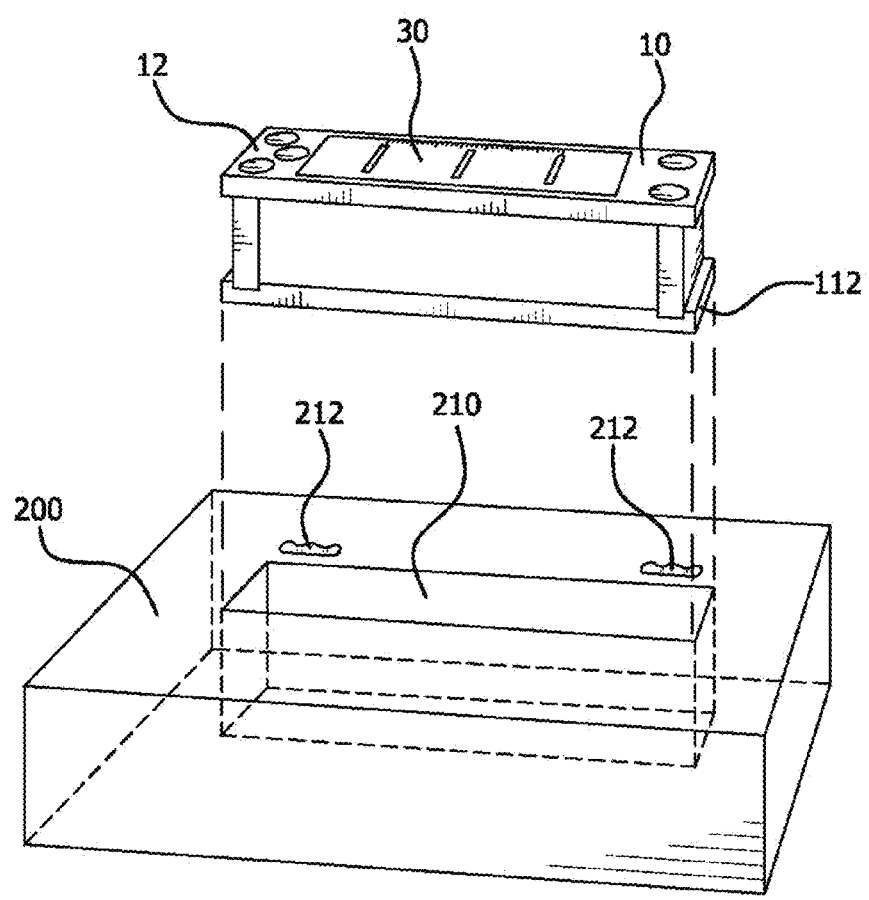
FIG. 6 shows a FMT holder compatible with a cassette.

In some preferred aspects, the cassette 10 may be used with a fluorescence molecular tomography (FMT) imager and a magnetic resonance (MR) imager 500. Thus, for example, a mouse 100 may be placed within the cassette 10, imaged in a FMT imager, kept in the same cassette 10, and imaged in a MR imager, without the need to remove or reposition the mouse 100 (the order of imagers is not critical, and the mouse 100 may be imaged within the cassette 10 in the MR imager before the FMT imager). In aspects where the FMT imager requires a larger holder than the cassette 10, the cassette 10 may be placed inside a chamber of a separate holder, removed from the holder following FMT imaging, and then placed inside a MR imager. For example, the cassette 10 may be adapted and/or configured in a manner to fit inside a tomographic imaging holder 200 as shown in FIG. 6. One example of such an imaging holder is described in U.S. Patent Application Publication No. 2011/0071388 (application Ser. No. 12/934,246). Thus, the imaging holder of U.S. Patent Application Publication No. 2011/0071388 may be modified to interchange the imaging window described in this document with the cassette 10.

In FIG. 6, the imaging holder 200 has a chamber 210 configured to house the cassette 10. The cassette 10 may friction fit in the chamber 210, or may be held in place by one or more fasteners 212 on the holder 200. The cassette 10 may be placed into the chamber 210 via an opening on any side of the holder 200. In some aspects, a gas such as an anesthetic gas or oxygen may be administered to the cassette 10 while the cassette 10 is present in the holder 200.

Figure 7:
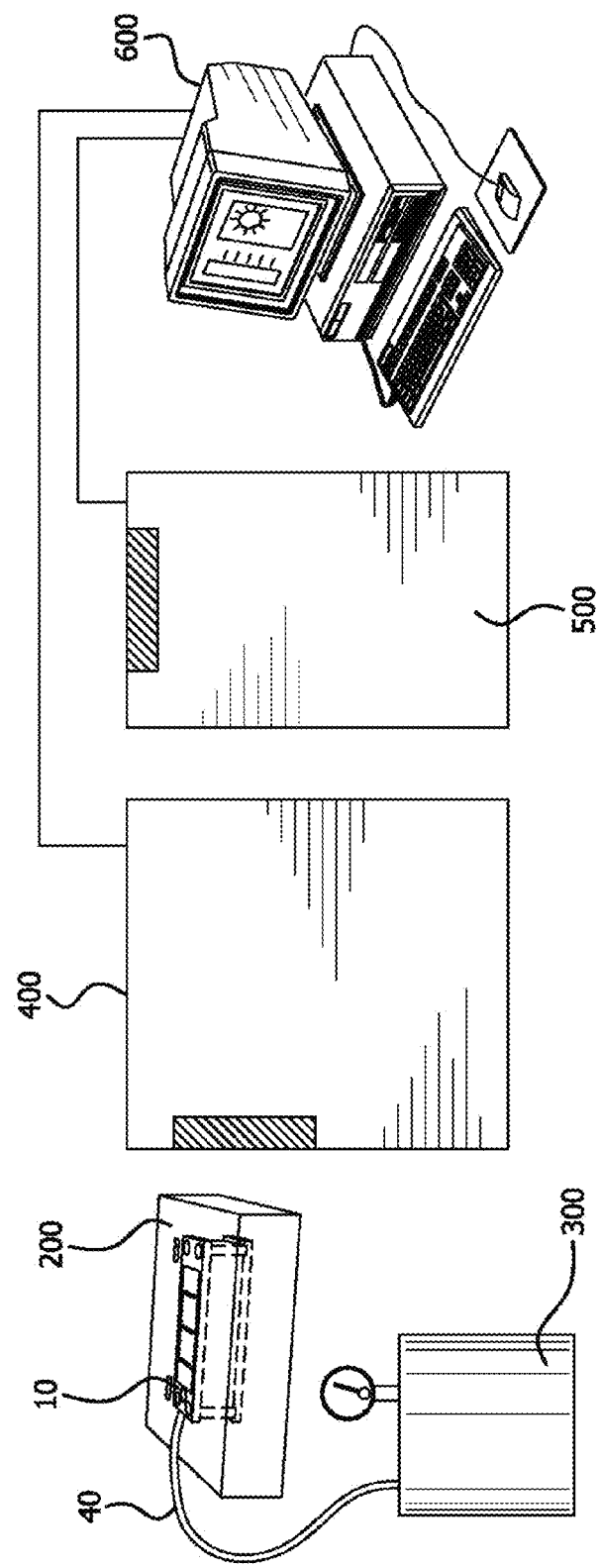
FIG. 7 shows a FMT and MRI imaging system.

The cassette 10 may be used in accordance with systems comprising one or more of the cassette 10, the holder 200, a gas source 300, a fluorescence molecular tomography imager 400, the magnetic resonance imager 500, and a processor 600. An example of such a system is shown in FIG. 7. The processor 600 may comprise executable code for causing the processor 600 to integrate image data generated from the fluorescence molecular tomography imager 400 and the magnetic resonance imager 500, and create images of a region of interest in the imaged animal. The gas source 300 may be an oxygen supply and/or a supply of anesthetic gases such as nitrous oxide sevoflurane, enflurane, desflurane, isoflurane, and halothane; air; heliox (mixture of helium and oxygen); nitrogen; or combinations of the listed gases. The gas source 300 may be a wall supply, or a tank, or an anesthesia gas machine.

FIG. 8 shows the FMT-MRI transfer cassette 10 with a mouse 100 and plastic fiducial markers 102 (left panel). The markers 102 are filled with a mixture of a fluorescent tag (VivoTag 680, Perkin Elmer inc.), and diluted Gd-DTPA (Magnevist, Berlex labs, Hamilton, N.J.). The markers 102 are visible in both FMT and MRI datasets, and form the references for point-based image fusion using the Amide software program (http://amide.sourceforge.net/index.html). In some aspects, the fiducial markers 102 are not implanted or otherwise administered to the inside of the animal. A belt 104 containing the same mixture of imaging agents as in the fiducial markers 102 may be placed around the midsection of the animal as a continuous set of co-registration points (right panel).

The cassette 10 and systems may be used in accordance with methods for imaging animals. In some aspects, the methods comprise imaging an animal to which an organ-specific label and one or more probes has been administered with a fluorescence molecular tomography (FMT) imager, imaging the animal with a magnetic resonance (MR) imager, and fusing the FMT and MR images. The methods may further comprise anesthetizing the animal. The one or more probes preferably comprises a detectable label.

In some aspects, the animal is a laboratory mammal, and in some preferred aspects, the animal is a mouse 100. The animal may spontaneously form tumors, or have a tumor implanted. The animal may be imaged in the FMT imager 400 and/or the MR imager 500 while housed in the cassette 10 such as described or exemplified this document. The cassette 10 may be in a holder 200. The MR imager 500 may be a vertical bore MR imager. The FMT and MR imagers 400, 500 may be part of a system such as those systems described in this document.

The organ-specific label may be any agent that localizes to a particular organ in the body of the animal substantially to the exclusion of other organs. The organ-specific agent may be, for example, a labeled polypeptide (e.g., a polypeptide comprising a detectable label), labeled ligand (e.g., a ligand comprising a detectable label), or labeled antibody (e.g., an antibody comprising a detectable label) that translocates to and specifically hybridizes, binds, or otherwise interacts with a receptor, antigen, molecule, marker, cell, or binding partner at the organ of interest. The organ-specific agent may be a labeled chemical agent (e.g., a chemical agent comprising a detectable label), or may be a chemical agent that itself is a detectable label or that is activated by enzymes in the organ of interest such that the label is detectable upon activation (e.g., cleavage) by enzymes. An organ-specific label may bind to, for example, phosphatidylserine in cells of the organ. The organ may be any organ in the body, including the kidneys as shown in the Examples below. AnnexinVivo 750 is one example of a chemical agent that localizes to the kidneys. Labeled organs may thus serve as an internal fiducial marker. In any case, a label is preferably a detectable label. A detectable label may comprise fluorochromes, radiolabels, enzymes, fluorescent proteins, and/or biotin.

In some aspects, the methods may optionally comprise administering to the animal an organ-specific label. The methods may optionally comprise administering to the animal one or more probes.

The organ-specific label and/or the probe may be administered to the animal according to any technique, at any location on or in the animal, and according to any time frame appropriate for the study. A plurality of organ-specific labels and/or probes may be administered, and may be administered one or more times, and at one or more time points. The probes may comprise one or more fiducial markers. The organ-specific label and/or the probe are preferably detectable by both FMT and MR imagers.

In some aspects, the methods comprise imaging an animal to which one or more fiducial markers have been attached and to which one or more probes has been administered with a fluorescence molecular tomography (FMT) imager, imaging the animal with a magnetic resonance (MR) imager, and fusing the FMT and MR images. The methods may further comprise anesthetizing the animal. The one or more fiducial markers may be attached to exterior of the animal according to any suitable technique, for example, by placing a band containing the fiducial markers (see, e.g., FIG. 8) around the body of the animal, or around a particular appendage of the animal, or around the head of the animal, or around the tail of the animal. The fiducial markers may be affixed to the position, for example, with an adhesive. The one or more fiducial markers may be implanted in the animal, including under the skin.

In some aspects, the animal is a laboratory mammal, and in some preferred aspects, the animal is mouse. The animal may spontaneously form tumors, or have a tumor implanted. The animal may be imaged in the FMT imager and/or the MR imager while housed in a cassette 10 such as a cassette 10 described or exemplified herein. The cassette 10 may be in a holder 200. The MR imager may be a vertical bore MR imager. The FMT and MR imagers may be part of a system such as those described herein.

In any of the methods described or exemplified herein, the one or more probes may be any labeled biomolecule or chemical agent that translocates to and specifically hybridizes, binds, or otherwise interacts with a receptor, antigen, molecule, marker, cell, or binding partner on, at, or proximal to a region of interest. For example, the probes may be specific to a cancer marker or antigen, such as an ovarian cancer marker. A cancer marker may comprise, for example, a cathepsin expressed in the tumor of interest. A cancer marker may comprise, for example, a matrix metalloproteinase expressed in a tumor of interest. A cancer marker may comprise, for example, an integrin expressed in a tumor of interest. An ovarian cancer marker may comprise, for example, a cathepsin expressed in ovarian cancer. An ovarian cancer marker may comprise, for example, a matrix metalloproteinase expressed in ovarian cancer. An ovarian cancer marker may comprise, for example, an integrin expressed in ovarian cancer. An integrin expressed in ovarian cancer may comprise alpha v beta 3.

A probe may be administered to the animal according to any technique, at any location on or in the animal, and according to any time frame appropriate for the study. A plurality of probes may be administered, and may be administered one or more times, and at one or more time points. The probes may comprise one or more fiducial markers. The probes may comprise a detectable label. A detectable label may comprise fluorochromes, radiolabels, enzymes, fluorescent proteins, and/or biotin. The probe is preferably detectable by both a FMT and MR imager.

In any of the methods described or exemplified in this document, fusing the FMT and MR images may be carried out according to any techniques suitable in the art. The images may be fused, for example, using processors and executable code such as software to combine and overlay the data set from each imaging analysis of the animal. The fused image may be three dimensional. The label may be quantified in the FMT image, the MR image, or the fused image, according to any techniques suitable in the art.

The labeled agents may be any organic or inorganic chemicals, or biomolecules, and all fragments, analogs, homologs, conjugates, and derivatives thereof. Biomolecules include proteins, polypeptides, nucleic acids, lipids, monosaccharides, polysaccharides, and all fragments, analogs, homologs, conjugates, and derivatives thereof. The labels may comprise fiducial markers.

The fiducial marker may comprise any organic or inorganic fluorophore, one or more fluorescent proteins such as GFP, RFP, BFP, YFP, an indocyanine dye, quantum dots, a visible-wavelength fluorophore, an infra-red fluorophore, an ultraviolet fluorophore, a superparamagnetic agent, luminous acrylic, and/or a radioisotope or radioactive agent. The marker may be present in a carrier such as water.

The invention also provides kits. A kit may, for example, be used to practice a method for imaging animals, including a method described or exemplified herein.

In some aspects, a kit may comprise an organ-specific label, one or more probes, and instructions for using the kit in a method for imaging animals. The organ-specific label may be any organ-specific label described or exemplified herein. A kidney-specific label is preferred. The one or more probes may be any probe described or exemplified herein. The probe preferably comprises a fiducial marker. The probe may bind to a cancer marker, and preferably binds to an ovarian cancer marker.

In some aspects, a kit may comprise a fiducial marker for attaching to the exterior of an animal, one or more probes, and instructions for using the kit in a method for imaging animals. The fiducial marker for attaching to the exterior of an animal may comprise a band, or materials for adhering to the skin, fur, or other external surface of the animal. The one or more probes may be any probe described or exemplified herein. The probe preferably comprises a fiducial marker. The probe may bind to a cancer marker, and preferably binds to an ovarian cancer marker.

The following examples are provided to describe the invention in greater detail. They are intended to illustrate, not to limit, the invention.

Example 1

Use of FMR-MRI Image Fusion to Measure the Concentration of Fluorescent Probes in a Genetically Modified Mouse Model of Ovarian Cancer Transgenic mice. TgMISIIR-TAg mice are a mouse line developed in house, which develop spontaneous ovarian tumors (Connolly, D. C. et al. (2003), Cancer Research 63:1389-97). TgMISIIR-TAg mice were genotyped by PCR amplification of the TAg transgene. Mice were maintained on a standard diet (2018SX Teklad Global, Harlan Laboratories, Somerville, N.J.) and transitioned to a purified, alfalfa free rodent chow (Teklad AIN-76A, Harlan Laboratories, Somerville, N.J.) for a minimum of 24 hours prior to fluorescent imaging to minimize fluorescence in the gut. Procedures were approved by the Fox Chase Cancer Center (FCCC) Institutional Animal Care and Use Committee, and mice were maintained under specific pathogen free conditions.

Optical imaging agents. For optical imaging of ovarian tumors and cells, commercially available imaging probes designed to detect oncologic processes were used. Tumor-associated cathepsin and matrix metalloproteinase (MMP) activities were detected with ProSense® or MMPSense®, respectively, and tumor-associated integrin receptor expression was detected with the integrin alpha v beta 3 ($\alpha v \beta 3$) targeted probe IntegriSense. AnnexinVivo 750, which detects exposed phosphatidylserine, was used for anatomic localization based on its retention in the kidneys. All probes were purchased from Perkin Elmer Inc., and were administered intravenously into anesthetized mice by retro-orbital injection at a dose of 2.0 nmoles for in vivo experiments.

FMT image acquisition. Fluorescence molecular tomography (FMT) was performed using the VisEn® FMT2500 imaging system (available from VisEn Medical, now Perkin Elmer Inc. Waltham, Mass.). In this system, mice are placed in a bi-planar imaging cassette, and then trans-illuminated with laser light. The resultant transmission and fluorescence patterns are captured with a thermo-electrically cooled Charge-Coupled Device (CCD) camera, and the position and intensity of fluorescence sources are reconstructed by modeling the propagation of the emitted photons through the intervening tissue. During the procedure mice are anesthetized with isoflurane (Isosol product available from Vedco, Inc. St. Joseph, Mo.), at a concentration of 2% in medical grade $O_2$). Prior to imaging, mice were anesthetized with isoflurane (Isosol, Vedco, Inc.) at a concentration of 2% in medical grade $O_2$ and fur around the lower thorax, abdomen and back was removed by shaving and depilation with a cosmetic hair removal lotion.

For this work, a variety of activated or targeted probes (ProSense®, MMPSense®, IntegriSense) were purchased from VisEn® Medical. Probes were injected according to the manufacturer's recommendations, with 2 nmoles of fluorescent probe delivered via retro-orbital injection and imaged 24 hours later in the 680 nm channel. In order to mark the kidneys for image fusion with magnetic resonance (MR), the probe Annexin-Vivo 750 was injected retro-orbitally and imaged 2 hours later in the 750 nm channel. Data were acquired using the normal (3 mm) source point image spacing with the excitation grid covering the entire abdominal section of the mouse (requiring approximately 80 separate points). Fluorescent sources were reconstructed in three dimensions with the Truequant software package supplied with the FMT2500. FMT imaging times totaled approximately 15 minutes.

Use of the image transfer cassette. MRI was performed in a vertical bore 7 Tesla magnet with a Bruker® DRX300 spectrometer and Paravision 3.0 software. Although the imaging cassette supplied with the FMT2500 is MR-compatible, due to the limited space in the 30 mm radiofrequency (RF) imaging coil, the imaging cassette could not be directly transferred into the RF coil. Instead, mice were placed in a transfer cassette according to the invention, constructed of a Lucite® frame and 0.12 mm thick Mylar® windows. Both cassettes compressed the mice to a thickness of 15.0 mm in the anterior-posterior direction. When moving the mouse from the FMT imaging cassette to the MRI cassette, care was taken to position it in precisely the same orientation, aligning the inferior-superior axis of the mouse parallel to the edges of the cassette. While compressed in the imaging cassettes, there was a tendency of the spine of the mouse to lie slightly to the left or right of the centerline, this was noted and the spine was aligned consistently in both cassettes.

Magnetic Resonance Imaging. The MR imaging protocol was previously published (Hensley H et. al (2007) Cancer Biol. Ther. 6:1717-25). In brief, an intramuscular injection of 0.2 ml Gd-DTPA (the Magnevist product available from Berlex labs, Wayne N.J., diluted 1:10 in sterile PBS) was given into the deltoid muscle. Mice were placed in the MR transfer cassette, which was then inserted into the RF coil, and then into the bore of the vertical magnet. After a series of scout scans in the axial and sagittal orientations, a set of coronal images were made with a conventional interleaved multi-slice spin echo pulse sequence with fat suppression (standard on Bruker DRX systems). Typical data sets were acquired with a slice thickness=0.75 mm, field of view=2.56 cm, matrix size of 256×256, with 4 signal averages and 12-15 slices, and repetition time=500-700 msec for a total scan time of approximately 9 minutes. In order to make redundant volume measurements, an axial data set covering the ovaries was acquired following the acquisition of the coronal data set. Mice remained under isoflurane anesthesia (1-2% in $O_2$) for the duration of the procedure.

MRI tumor volume measurement. For generating tumor volumetrics, the MR image data sets were first converted to Analyzer™ image format, and then analyzed using the freeware program MRIcro (http://www.psychology.nottingham.ac.uk/staff/cr1/mricro.html). To determine the volume of ovarian tumors present in the mice, each data set was reviewed and regions of interest (ROI) defined as the ovary (and/or tumor) were identified and highlighted on each section. The ROIs corresponding to the right and left ovaries were defined individually and the volume for each ovary calculated by multiplying the voxel volume by the total number of voxels defined for each ovary in all ROIs using the formula: (X)(Y)(Z)(nROI), where X and Y=in-plane voxel dimensions, and Z=section thickness, and nROI=number of voxels defined in all ROIs for each ovary. The voxel size (0.1 mm×0.1 mm×0.75 mm) provided sufficient contrast to noise and spatial resolution for the measurement of the normal ovaries that are typically <10 $mm^3$.

Image fusion. FMT and MR volumetric data sets were fused with the freely available AMIDE software package (Loening, Gambhir, UCLA). The Truequant software permitted exportation of the FMT datasets in DICOM format, while the MR datasets were imported directly into Amide, with the relevant scan geometry information entered manually. Image fusion of the two modalities was done using the kidneys as internal fiducial markers. The datasets were aligned and rotated until the kidneys (as detected in the 750 nm channel of the FMT system) overlapped with the kidneys in the MR dataset in three dimensions. The same transformations that aligned the kidneys in the 2 datasets were then applied to the FMT dataset from the 680 nm channel. The position of the ovaries (or ovarian tumors) relative to the kidneys in the MR data set was noted, as was any signal in the 680 nm channel overlapping with, or in close proximity to, the ovaries (or ovarian tumors). These regions were then identified on the FMT datasets as displayed in the Truequant software. In order to measure the absolute value of probe retention in pmoles, (a value calculated by Truequant), regions of interest of similar volume to that calculated directly from the MR datasets were drawn around the ovary signals in the FMT data set. Examples of fused images are shown in FIG. 9 and FIG. 10.

Figure 9:
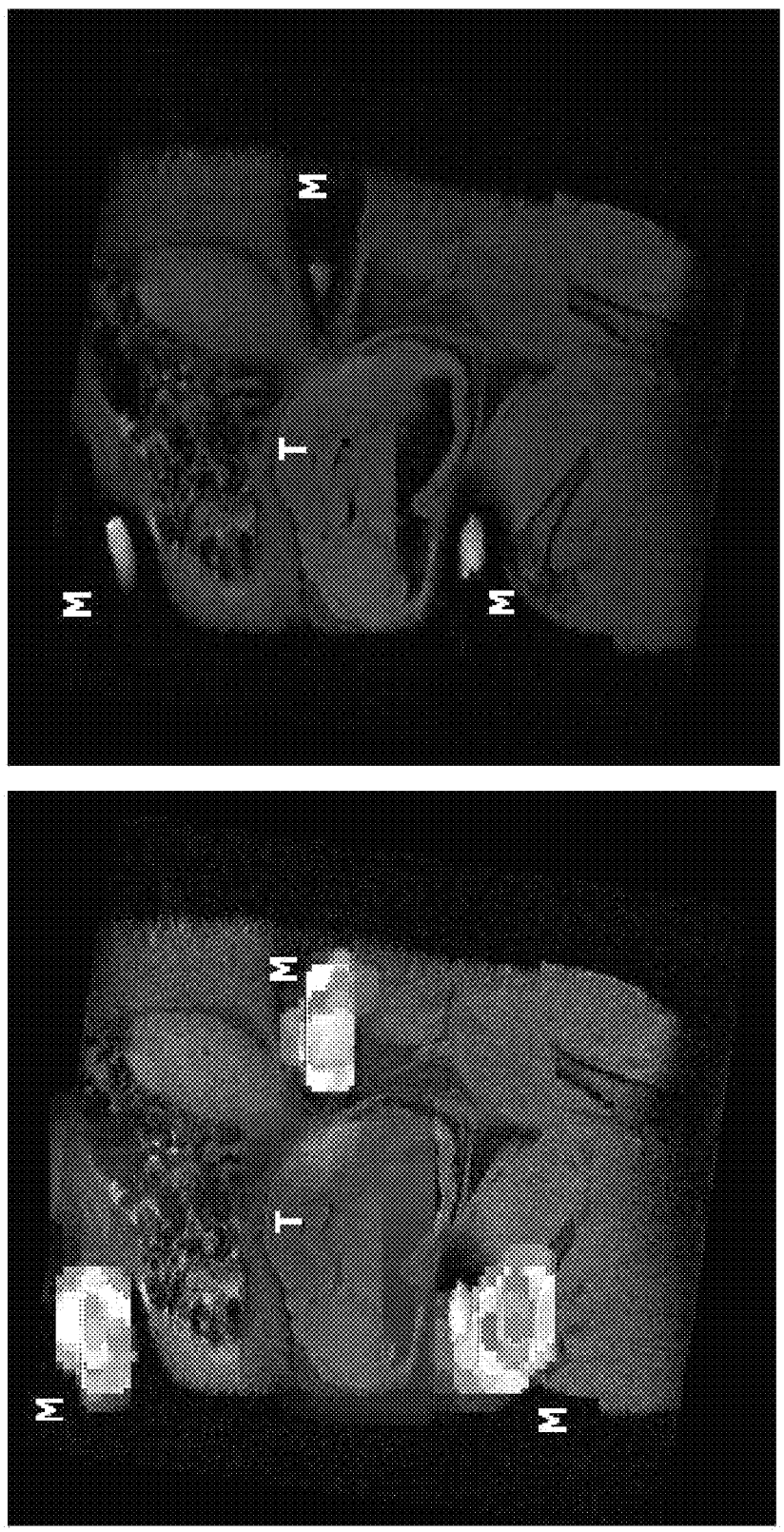
FIG. 9 shows images demonstrating the appearance of the fiducial markers in a fused MRI/FMT dataset (left panel) and the MRI slice from the same dataset (right panel).

Specifically, FIG. 9 shows an image from a fused MRI/FMT dataset (left panel). GIST tumor xenografts were imaged with Annexin-Vivo 750 (Perkin Elmer) and labeled "T." The MRI slice from the same dataset is shown in the right panel. The signal from the VivoTag® 680 in the markers is labeled "M." The markers and tumor are clearly visible in the MR image.

Figure 10:
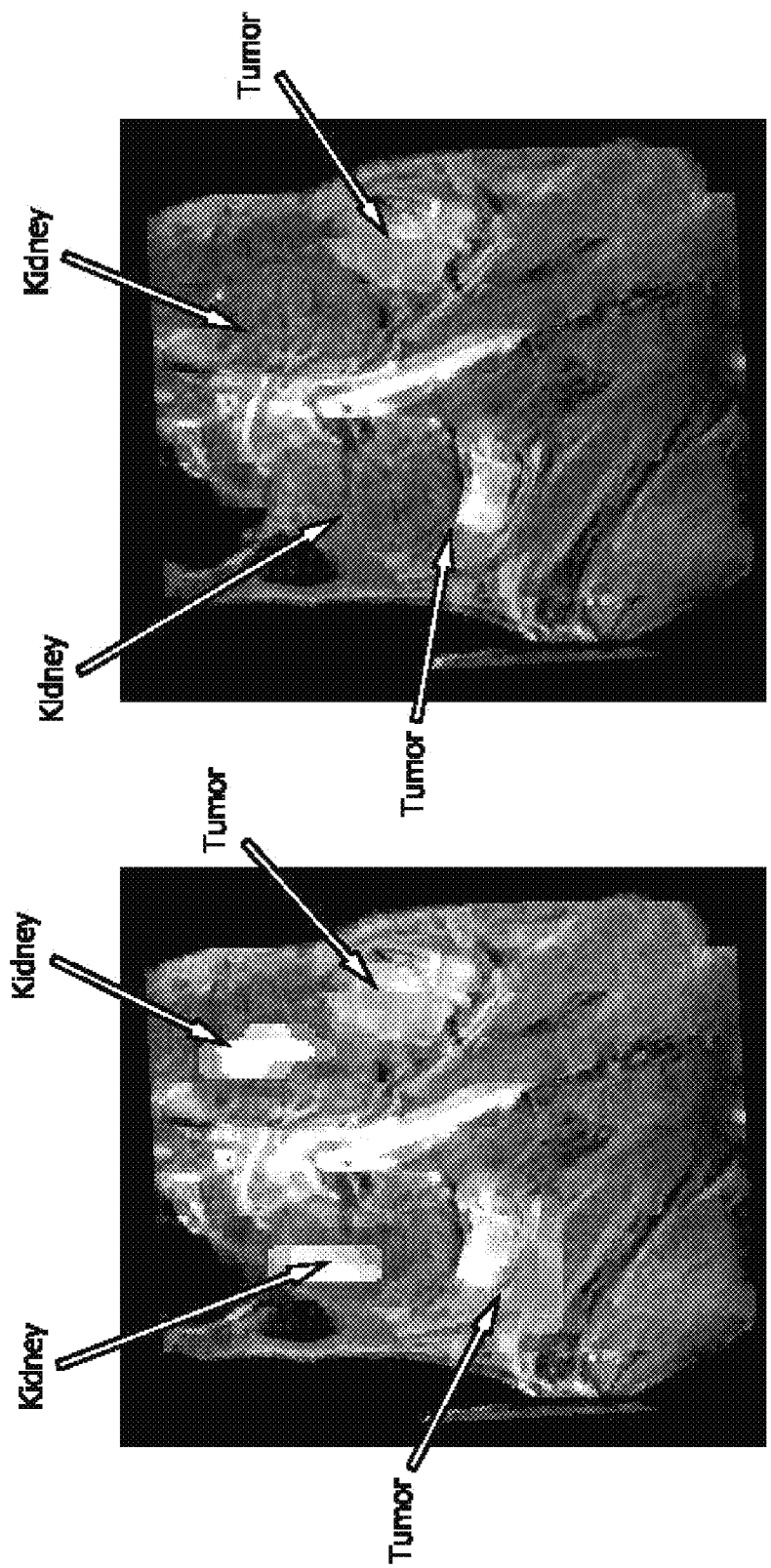
FIG. 10 shows a fused dataset in a mouse with spontaneous ovarian tumors (left panel) and the MRI dataset (right panel), illustrating the use of the kidney as an internal fiducial marker.

FIG. 10 shows a fused dataset in the mouse 100 with spontaneous ovarian tumors (left panel). Annexin-Vivo 750 dye localized strongly to the kidneys (labeled "K") (left panel); the kidneys are also easily found on the MRI dataset (right panel). The ProSense® 680 localizes to the ovarian tumors ("T") located just below the kidneys. The kidneys therefore serve as an internal fiducial marker in close proximity to the ovarian tumors.

Ex-vivo. Following MR imaging, animals were euthanized. The abdominal cavity was exposed and imaged in an IVIS spectrum (Caiperls Hopkinton, Mass.). The 680 nm probes were imaged with an excitation wavelength of 640 nm and detected at 700 nm, while the Annexin-Vivo 750 was imaged with excitation=710 nm, detection=760 nm. Thereafter, excised organs (ovaries, kidney, intestine, liver, and spleen) were imaged in the IVIS spectrum with the same parameters as the exposed organs. Ex vivo fluorescence images of the exposed abdominal cavity and dissected organs confirmed the presence of fluorescent signals from AnnexinVivo 750 in the kidneys and ProSense® 680, Integrisense 680, or MMPSense® 680 (depending on the experiment) in the ovaries. Regions of interest were drawn around each ovarian tumor, and the total radiant efficiency as calculated by the Living Image software (supplied with IVIS spectrum) was recorded. Caliper measurements of tumor size in three orthogonal dimensions were taken at this time. Ovarian tumors were fixed in neutral buffer formalin for histopathological assessment.

Example 2

Image Fusion Validation

FIG. 11 shows the application of the methods described in Example 1 for determining the concentration of Prosense®

680 in a large ovarian tumor. FIG. 11A shows a mid-coronal slice through the MRI dataset with the tumor and kidneys labeled. FIG. 11B shows the FMT dataset in the same spatial plane, with the Prosense® 680 signal from the instrument's 680 nm channel concentrated in the tumor, and the AnnexinVivo 750 signal from the instrument's 750 nm channel. FIG. 11C shows an overlay of the MRI and FMT signals, showing good co-localization of the reconstructed fluorescent signals and anatomy from MRI.

Figures 12A, 12B, 12C:
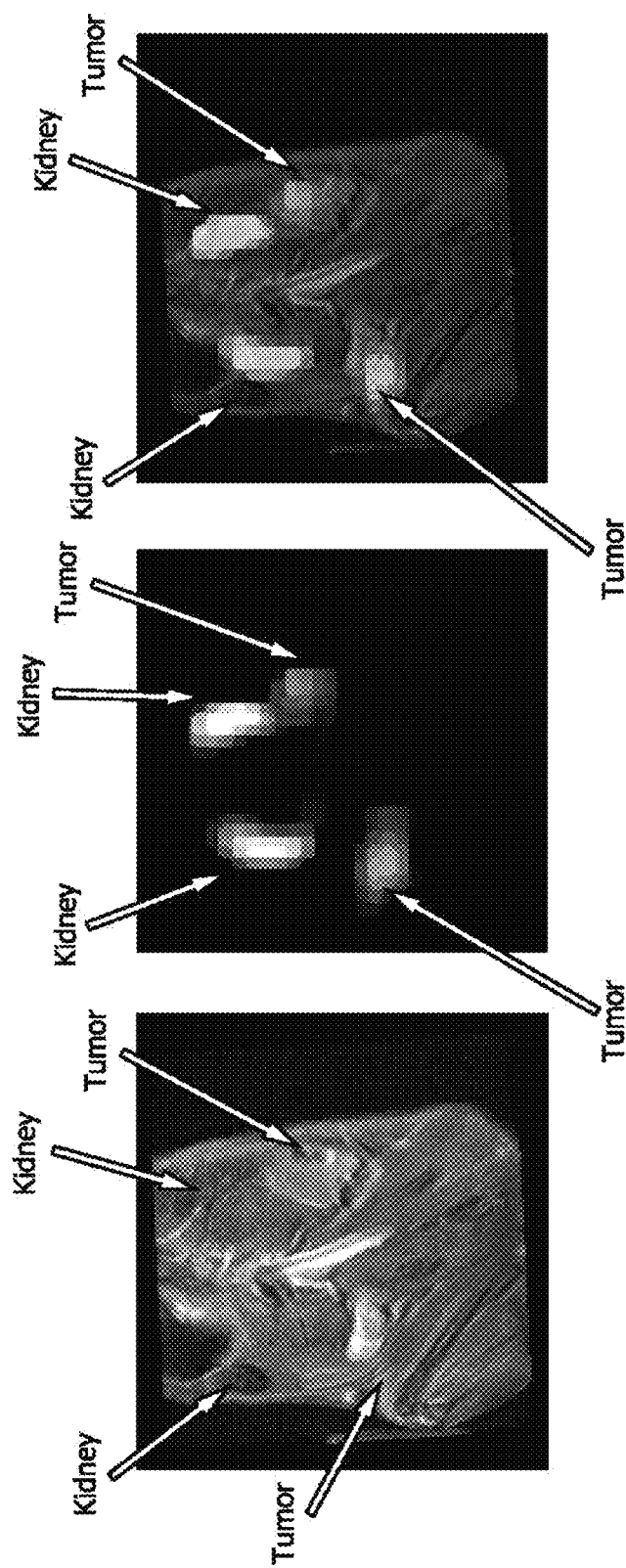
FIGS. 12A-12C show another alignment of MR and FMT images using AnnexinVivo 750. The MR and fluorescent FMT images from a TgMISIIR-TAg (TAg+) mouse bearing bilateral ovarian tumors injected with ProSense® 680 and AnnexinVivo were aligned using AMIDE™ software.

FIG. 12 shows the application of the methods for detecting and measuring the Prosense® 680 concentration in two small, bilateral tumors in a different transgenic mouse. MRI (FIG. 12A), FMT (FIG. 12B) and FMT-MRI fusion (FIG. 12C) images are labeled the same way they were labeled in FIG. 11.

Figures 13A, 13B, 13C:
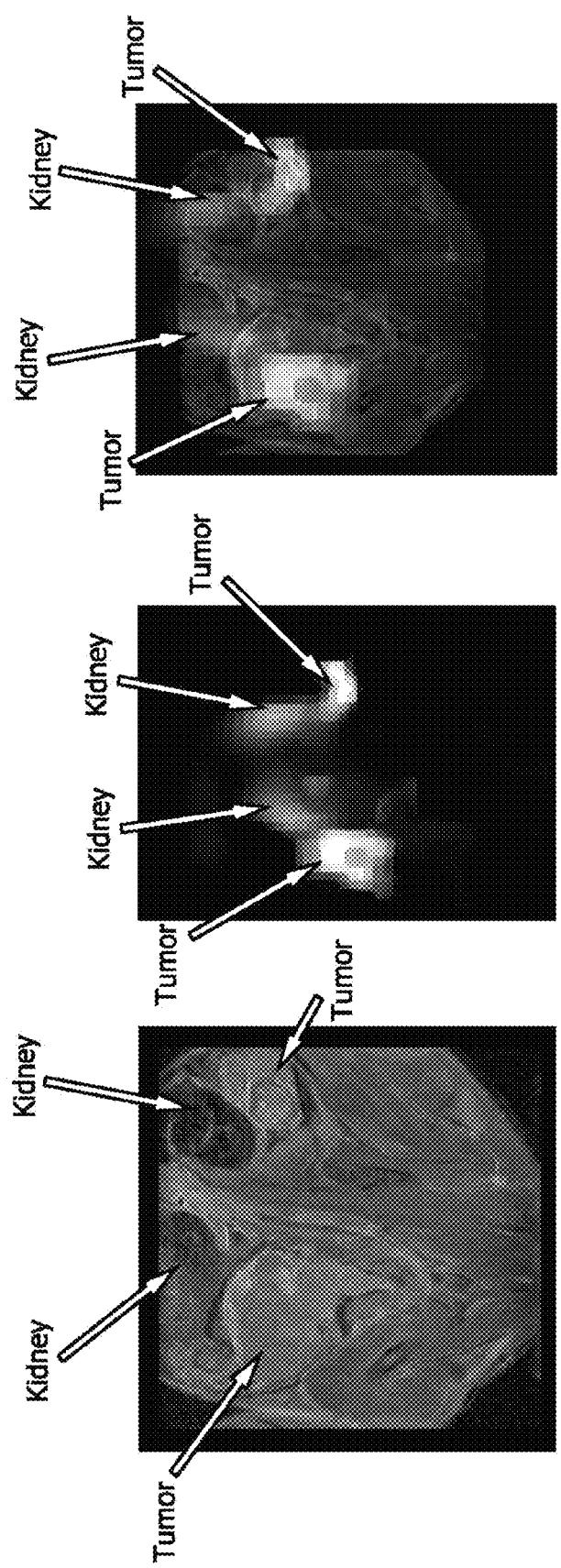
FIGS. 13A-13C show another alignment of MR and FMT images using AnnexinVivo 750 and the ovaries detected by the imaging agent Integrisense. The MR and fluorescent FMT images from a TgMISIIR-TAg (TAg+) mouse bearing bilateral ovarian tumors injected with Integrisense 680 and AnnexinVivo were aligned using AMIDE.

FIG. 13 shows the detection of the Intregrisense 680 in two relatively large bilateral ovarian tumors, with MRI (FIG. 13A), FMT (FIG. 13B) and FMT-MRI fusion (FIG. 13C) images labeled as in FIG. 11.

Figures 14A, 14B:
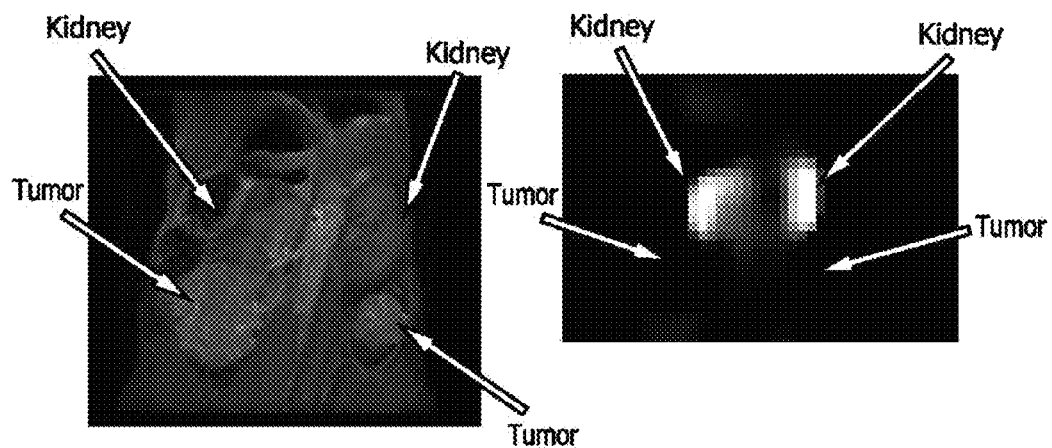
FIGS. 14A-14D show another alignment of MR and FMT images using AnnexinVivo 750 and the ovaries detected by the imaging agent MMPsense® 680. The MR and fluorescent FMT images from a TgMISIIR-TAg (TAg+) mouse bearing bilateral ovarian tumors injected with MMPsense® 680 and AnnexinVivo were aligned using AMIDE™ software. In the case the probe was distribute widely throughout the abdomen of the mouse, however the anatomical information from the MRI dataset allowed the determination of the probe concentration in the ovarian tumors.
Figures 14C, 14D:
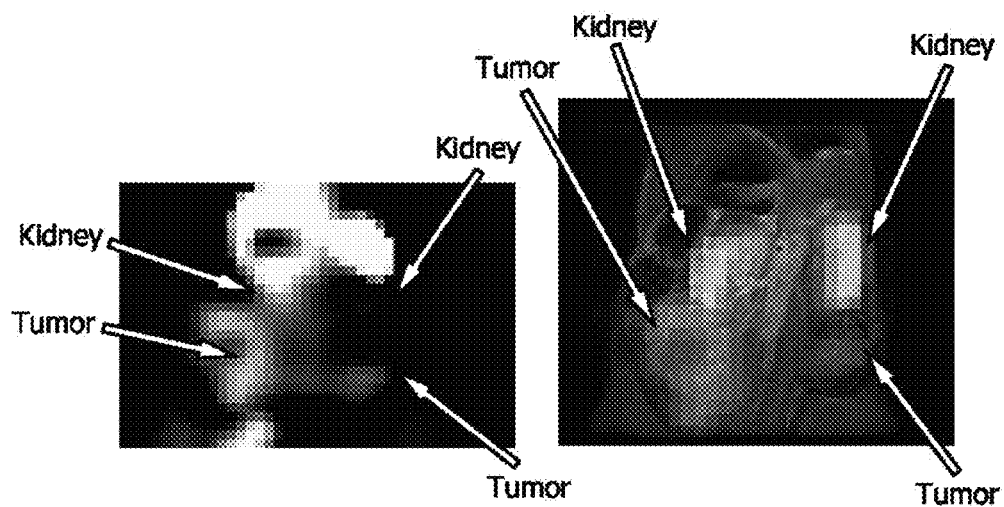

FIG. 14 shows the application of the methods for detecting and measuring the MMPsense® 680 concentration in two bilateral tumors. The MRI image is shown in FIG. 14A. FIG. 14B shows the AnnexinVivo 750 signal in the kidneys. Because the MMPsense® 680 showed a large signal in the liver which tended to overlap with and obscure the kidney signal (although since the different fluorophores are imaged in different FMT optical channels the signals are separable in the Truquant system), only the MMPsense® 680 signal is shown in FIG. 14C. The overlay in FIG. 14D shows the co-localization of the AnnexinVivo 750 signal with the kidneys. The MMPsense® 680 signal was chosen manually by taking a region of interest from the anatomical MRI system corresponding to the tumor. This illustrates that even if probes do not localize exclusively to the tumors, the anatomic information from the MRI images can be used to determine the tumor location in the FMT images.

The invention is not limited to the embodiments described and exemplified above, but is capable of variation and modification within the scope of the appended claims.

We claim:

1. A method for imaging a tumor in an animal, comprising
(a) labeling an organ in the animal with a first detectable label that localizes substantially exclusively to the organ by specifically hybridizing or binding with a receptor or antigen at the organ, whereupon the labeled organ is capable of use as a first fiducial marker in an image of the animal and the first detectable label is detectable by both fluorescence molecular tomography (FMT) and magnetic resonance (MR);
(b) administering to the animal one or more detectably labeled probes that localize substantially exclusively to a region of interest in the body of the animal separate from the labeled organ;
(c) after labeling the organ according to step (a) and administering the one or more detectably labeled probes according to step (b), imaging the animal with a FMT imager to generate an FMT image, and imaging the animal with a MR imager to generate an MR image; and
(d) aligning the FMT image and MR image using the first fiducial marker as a first reference point in the FMT image and in the MR image, thereby generating an image comprising a fusion of the FMT image and the MR image.

2. The method of claim 1, wherein the organ is a kidney.

3. The method of claim 1, wherein the region of interest is an ovarian cancer tumor having a marker, and the marker includes one or more of a cathepsin, a matrix metalloproteinase, or an integrin expressed by an ovarian cancer cell.

4. The method of claim 3, wherein the integrin is alpha v beta 3.

5. The method of claim 1, wherein the MR imager is a vertical bore MR imager.

6. The method of claim 1, wherein during the imaging of step (c), the animal is housed in a cassette.

7. The method of claim 1, wherein the image comprising a fusion of the FMT image and the MR image is three dimensional.

8. The method of claim 1, wherein the animal is a mouse.

* * * * *